United States Patent
Jackson et al.

(10) Patent No.: US 6,372,741 B1
(45) Date of Patent: *Apr. 16, 2002

(54) USE OF CSAID™ COMPOUNDS AS INHIBITORS OF ANGIOGENESIS

(75) Inventors: Jeffrey R. Jackson, Collegeville; James D. Winkler, Fort Washington, both of PA (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/142,485
(22) PCT Filed: Mar. 7, 1997
(86) PCT No.: PCT/US97/03626
  § 371 Date: Sep. 8, 1998
  § 102(e) Date: Sep. 8, 1998
(87) PCT Pub. No.: WO97/32583
  PCT Pub. Date: Sep. 12, 1997

Related U.S. Application Data
(60) Provisional application No. 60/013,138, filed on Mar. 8, 1996.

(51) Int. Cl.⁷ ............... A61K 31/4178; A61K 31/4164
(52) U.S. Cl. ............... 514/235.8; 514/252; 544/122; 544/123; 544/316; 544/331
(58) Field of Search ............... 544/122, 123, 544/316, 331; 514/235.8, 252

(56) References Cited

U.S. PATENT DOCUMENTS

| | | | |
|---|---|---|---|
| 4,808,402 A | 2/1989 | Leibovich et al. | 424/423 |
| 5,525,604 A | 6/1996 | Lee et al. | 514/256 |
| 5,525,724 A | 6/1996 | Hunds | 544/334 |
| 5,593,992 A | * 1/1997 | Adams et al. | 514/235.8 |
| 5,658,903 A | * 8/1997 | Adams et al. | 514/235.8 |
| 6,046,208 A | * 4/2000 | Adams et al. | 514/274 |

FOREIGN PATENT DOCUMENTS

| | | |
|---|---|---|
| WO | WO93/14081 | 7/1993 |
| WO | WO93/14082 | 7/1993 |
| WO | WO 95/02591 | * 1/1995 |
| WO | WO95/09841 | 4/1995 |
| WO | WO95/31451 | 11/1995 |

OTHER PUBLICATIONS

Soni Chem. Abstract 97:216082., 1982.*
Ben Ezra et al., "In vivo angiogenetic activity of interleukins", *Archives of Ophthalmology*, 108(4), pp. 573–576 (1990).

* cited by examiner

*Primary Examiner*—Richard L. Raymond
*Assistant Examiner*—Deepak R. Rao
(74) *Attorney, Agent, or Firm*—Dara L. Dinner; Stephen Venetianer; Charles M. Kinzig

(57) ABSTRACT

The present invention is to the novel use of a cytokine inhibitor, which cytokine is inhibited by the inhibition of the kinase CSBP/p38/RK, for the treatment of chronic diseases which are caused by excessive, undesired or inappropriate angiogenesis.

11 Claims, 6 Drawing Sheets

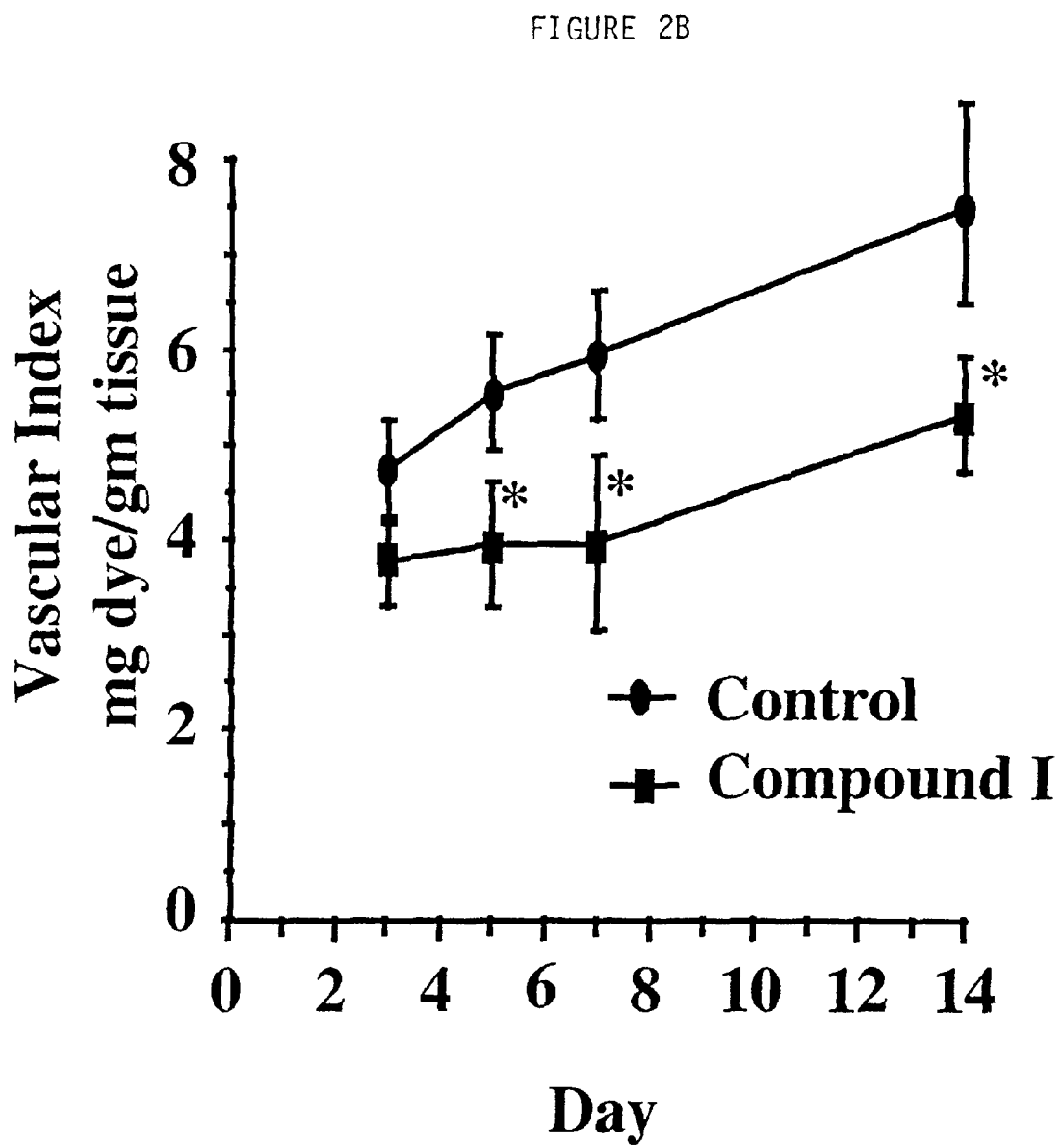

USE OF CSAID™ COMPOUNDS AS INHIBITORS OF ANGIOGENESIS

This application is the §371 national stage entry of PCT/US97/03626, filed Mar. 7, 1997 which claims the benefit of U.S. Ser. No. 60/013,138 filed Mar. 8, 1996.

FIELD OF THE INVENTION

The present invention relates to the treatment of diseases, in a mammal, in which inappropriate, excessive or undesirable angiogenesis has occurred.

BACKGROUND OF THE INVENTION

Chronic diseases are often accompanied by profound angiogenesis, which can contribute to or maintain an inflammatory and/or proliferative state, or which leads to tissue destruction through the invasive proliferation of blood vessels. EL-1β and TNFα have been found to be potent inducers of angiogenesis in vivo and are commonly involved in the pathology of chronic inflammatory diseases (Folkman and Shing, J. Biol. Chem. 267:10931, 1992).

Angiogenesis is generally used to describe the development of new or replacement blood vessels, or neovascularisaflon. It is a necessary and physiologically normal process by which the vasculature is established in the embryo. Angiogenesis does not occur, in general, in the normal adult. Many diseases, however, are characterized by persistent and unregulated angiogenesis. For instance, in arthritis, new capillary blood vessels invade the joint and destroy cartilage (Colville-Nash and Scott, Ann. Rheum. Dis., 51, 919,1992). In diabetes, new vessels invade the vitreous and blood, and cause blindness (and may occur in many different eye diseases) (Brooks et al., Cell, 79, 1157, 1994). The process of atherosclerosis has been linked to angiogenesis (Kahlon et al., Can. J. Cardiol. 8, 60, 1992). Tumor growth and metasis have been found to be angiogenesis-dependent (Folkman, Cancer Biol, 3, 65, 1992; Denekamp, Br. J. Rad. 66, 181, 1993; Fidler and Ellis, Cell, 79, 185, 1994).

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis (O'Reilly et al., Cell, 79, 315, 1994; Ingber et al., Nature, 348, 555, 1990), ocular diseases (Friedlander et al., Science, 270, 1500, 1995), arthritis (Peacock et al., J. Exp. Med. 175, 1135, 1992; Peacock et al., Cell. Immun. 160, 178, 1995) and hemangioma (Taraboletti et al., J. Natl. Cancer Inst. 87, 293, 1995).

A need still exists, however, to find suitable small molecule inhibitors which will block angiogenesis in a mammal for treatment of these diseases which have an angiogenic component. The current application teaches the novel finding that CSAID™ compounds, i.e. compounds that block cytokine production, can block angiogenesis by removing the early cytokine signals for angiogenesis.

SUMMARY OF THE INVENTION

The present invention is to the novel use of a cytokine inhibitor for the treatment of chronic inflammatory or proliferative or angiogenic diseases which are caused by excessive, inappropriate angiogenesis. The preferred compounds for use as cytokine inhibitors are those compounds of Formula (I) as noted herein. The preferred method of inhibition is the inhibition of the CSBP/p38/RK kinase pathway.

BRIEF DESCRIPTION OF THE DRAWINGS

FIGS. 2A–2D demonstrate the time course of granuloma development in murine air pouch angiogenesis model. Animals were orally dosed twice daily with either vehicle or 30 mg/kg compound I from Day 0 until removal of granuloma tissue at days 3, 5, 7, or 14. Granuloma size was determined by dry weight to control for possible differences in edema, A. Vascular index (mg carmine dye/gm dry tissue) was determined as described above, B. TNF-α levels within granuloma were determined by ELISA on tissue homogenates, C. IL-1β levels were determined by ELISA in the same tissue homogenates as C, D. Data are shown as mean +/− S.D., n=5. * significant from control at p<0.05, ** significant from control at p<0.01, calculated by Duncan's multiple range test.

DETAILED DESCRIPTION OF THE INVENTION

Figure 1A:
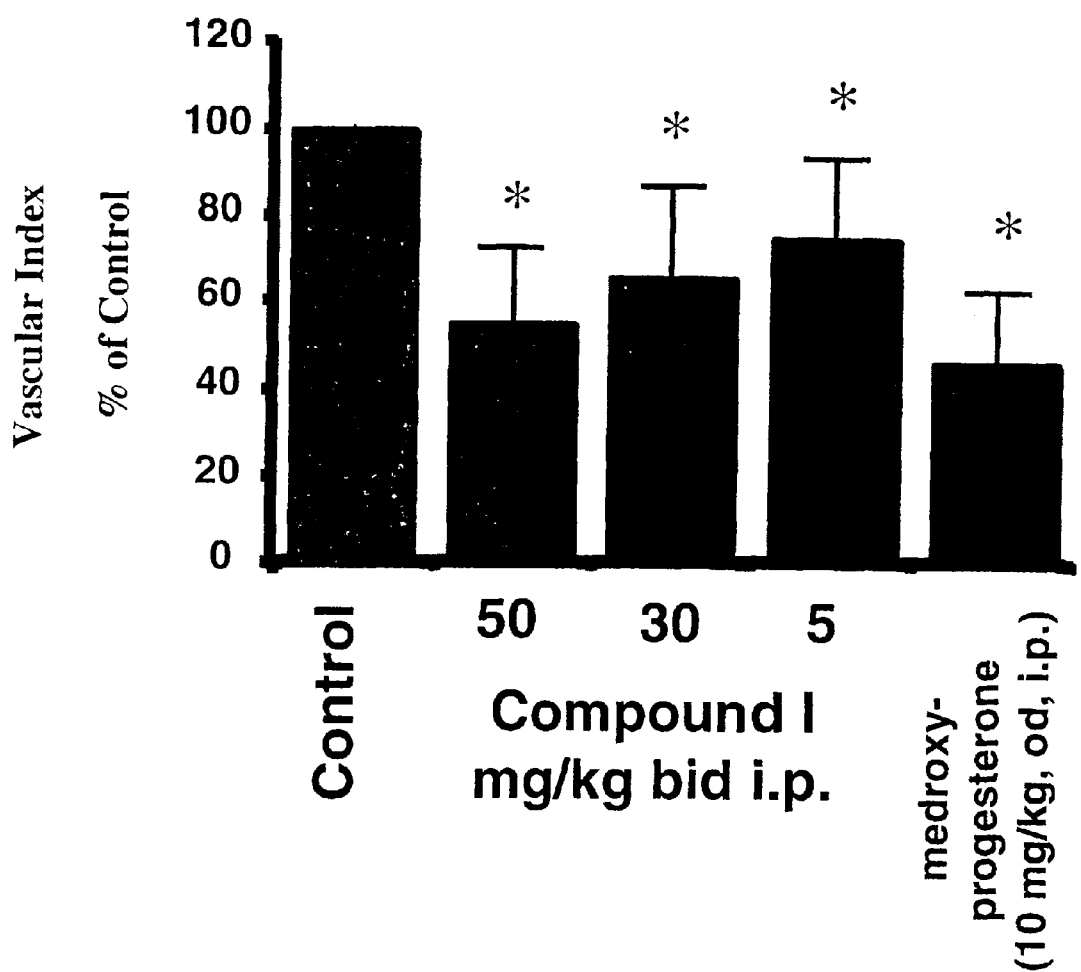
FIGS. 1A and 1B demonstrate the effects of Compound I, [1-Piperidine-4-(4-fluorophenyl)-5-(2-aminopyrimidin-4-yl)imidazole] on tissue dry weight and vascular index (mg carmine dye/gm dry tissue) of Day 6 granulomas following treatment with compound I or medroxyprogesterone. Dosing began at the time granulomas were induced. Data is expressed as a percent of vehicle treated control animals +/− S.D. Control VI=5.4. control dry weight=0.28 gms. n=5. * significant from control at p<0.05, calculated by Duncan's multiple range test.

The present invention is to the novel use of a cytokine inhibitor, in particular that of cytokine CSBP/p38, for the treatment of chronic inflammatory diseases which are caused by excessive or inappropriate angiogenesis.

Compounds for use herein include the cytokine inhibitors as described in U.S. Ser. No. 08/091,491, published as WO95/02575; WO96/21452; U.S. Ser. No. 08/369,964; U.S. Ser. No. 08/473,396; U.S. Ser. No. 08/659,102; U.S. Ser. No. 08/764,003; WO96/40143; U.S. Ser. No. 08/473,398; WO96/21654; WO93/14081; U.S. Ser. No. 08/095,234; WO95/03297; U.S. Ser. No. 08/481,671; PCT/US97/100619; PCT/US97/00614; PCT/US97/00500; PCT/US97/00529; U.S. Ser. No. 60/013,357; U.S. Ser. No. 60/013,358; U.S. Ser. No. 60/013,359; WO93/14082; WO95/13067; and WO95/31451. Each of these references are incorporated by reference herein in their entirety.

Preferred compounds for use as cytokine inhibitors are those compounds of Formula (I) as noted herein. Synthetic chemistry and methods of pharmaceutical formulations thereof are also contained within each noted patent application. A description of the assay for inhibition of the cytokine specific binding protein (CSBP) is also found in WO95/07922, whose disclosure is incorporated by reference in its entirety.

A preferred group of compounds for use herein are those compounds of the formula:

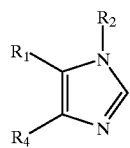

(I)

wherein:
R₁ is 4-pyridyl, pyrimidinyl, quinolyl, isoquinolinyl, quinazolin-4-yl, 1-imidazolyl or 1-benzimidazolyl, which heteroaryl ring is optionally substituted independently one to three times with Y, NHR$_a$, optionally substituted C$_{1-4}$ alkyl, halogen, hydroxyl, optionally substituted C$_{1-4}$ alkoxy, optionally substituted C$_{1-4}$ alkylthio, C$_{1-4}$ alkylsulfinyl, CH$_2$OR$_{12}$, amino, mono and di-C$_{1-6}$ alkyl substituted amino, or N(R$_{10}$)C(O)R$_b$;
Y is O—R$_a$;
R₄ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, —C(Z)NR₇R₁₇, —C(Z)OR₁₆, —(CR₁₀R₂₀)$_v$COR₁₂, —SR₅, —SOR₅, —OR₁₂, halo-substituted-C$_{1-4}$ alkyl, C$_{1-4}$ alkyl, —ZC(Z)R₁₂, —NR₁₀C(Z)R₁₆, or —(CR₁₀R₂₀)$_v$NR₁₀R₂₀ and which, for other positions of substitution, is halogen, cyano, —C(Z)NR₁₃R₁₄, —C(Z)OR₁₃, —(CR₁₀R₂₀)$_{m''}$COR₃, —S(O)$_m$R₃, —OR₃, halo-substituted-C$_{1-4}$ alkyl, —C$_{1-4}$ alkyl, —(CR₁₀R₂₀)$_{m''}$NR₁₀C(Z)₃, —NR₁₀S(O)$_m$R₈, —NR₁₀S(O)$_m$NR₇R₁₇, —ZC(Z)₃ or —(CR₁₀R₂₀)$_{m''}$NR₁₃R₁₄;
v is 0, or an integer having a value of 1 or 2;
m is 0, or the integer 1 or 2;
m' is an integer having a value of 1 or 2,
m" is 0, or an integer having a value of 1 to 5;
R₂ is C$_{1-10}$ alkyl N₃, —(CR₁₀R₂₀)$_n$OR₉, heterocyclyl, heterocyclylC$_{1-10}$ alkyl, C$_{1-10}$alkyl, halo-substituted C$_{1-10}$ alkyl, C$_{2-10}$ alkenyl, C$_{2-10}$ alkynyl, C$_{3-7}$ cycloalkyl, C$_{3-7}$cycloalkylC$_{1-10}$ alkyl, C$_{5-7}$ cycloalkenyl, C$_{5-7}$ cycloalkenyl C$_{1-10}$alkyl, aryl, arylC$^{1-10}$ alkyl, heteroaryl, heteroarylC$_{1-10}$alkyl, (CR₁₀R₂₀)$_n$OR₁₁, (CR₁₀R₂₀)$_n$S(O)$_m$R₁₈, (CR₁₀R₂₀)$_n$NHS(O)$_2$R₁₈, (CR₁₀R₂₀)$_n$NR₁₃R₁₄, (CR₁₀R₂₀)$_n$NO₂, (CR₁₀R₂₀)$_n$CN, (CR₁₀R₂₀)$_{n'}$SO₂R₁₈, (CR₁₀R₂₀)$_n$S(O)$_m$NR₁₃R₁₄, (CR₁₀R₂₀)$_n$C(Z)₁₁, (CR₁₀R₂₀)$_n$OC(Z)₁₁, (CR₁₀R₂₀)$_n$C(Z)OR₁₁, (CR₁₀R₂₀)$_n$C(Z)NR₁₃R₁₄, (CR₁₀R₂₀)$_n$C(Z)NR₁₁OR₉, (CR₁₀R₂₀)$_n$NR₁₀C(Z)R₁₁, (CR₁₀R₂₀)$_n$NR₁₀C(Z)NR₁₃R₁₄, (CR₁₀R₂₀)$_n$N(OR₆)C(Z)NR₁₃R₁₄, (CR₁₀R₂₀)$_n$N(OR₆)C(Z)R₁₁, (CR₁₀R₂₀)$_n$C(=NOR₆)R₁₁, (CR₁₀R₂₀)$_n$NR₁₀C(=NR₉)NR₁₃R₁₄, (CR$_{10R20}$)$_n$OC(Z)NR₁₃R₁₄, (CR₁₀R₂₀)$_n$NR₁₀C(Z)NR₁₃R₁₄, (CR₁₀R₂₀)$_n$NR₁₀C(Z)OR₁₀, 5-(R₁₈)-1,2,4-oxadizaol-3-yl or 4-(R₁₂)-5-(R₁₈R₁₉)-4,5-dihydro-1,2,4-oxadiazol-3-yl; wherein the aryl, arylalkyl, heteroaryl, heteroaryl alkyl, heterocyclic and heterocylic alkyl groups may be optionally substituted;
n is an integer having a value of 1 to 10;
n' is 0, or an integer having a value of 1 to 10;
Z is oxygen or sulfur;
R$_a$ is C$_{1-6}$alkyl, aryl, arylC$_{1-6}$alkyl, heterocyclic, heterocyclylC$_{1-6}$ alkyl, heteroaryl, or heteroarylC$_{1-6}$alkyl, wherein each of these moieties may be optionally substituted;
R$_b$ is hydrogen, C$_{1-6}$ alkyl, C$_{3-7}$ cycloalkyl, aryl, aryl$_{14-4}$ alkyl, heteroaryl, heteroarylC$_{1-4}$alkyl, heterocyclyl, or heterocyclylC$_{1-4}$ alkyl;
R₃ is heterocyclyl. heterocyclylC$_{1-10}$ alkyl or R₈;
R₅ is hydrogen, C$_{1-4}$ alkyl, C$_{2-4}$ alkenyl, C$_{2-4}$ alkynyl or NR₇R₁₇, excluding the moieties —SR₅ being —SNR₇R₁₇ and —SOR₅ being —SOH;
R₆ is hydrogen, a pharmaceutically acceptable cation, C$_{1-10}$ alkyl, C$_{3-7}$ cycloalkyl, aryl, arylC$_{1-4}$ alkyl, heteroaryl, heteroarylC$_{1-4}$ alkyl, heterocyclic, aroyl, or C$_{1-10}$ alkanoyl;
R₇ and R₁₇ is each independently selected from hydrogen or C$_{1-4}$ alkyl or R₇ and R₁₇ together with the nitrogen to which they are attached form a heterocyclic ring of 5 to 7 members which ring optionally contains an additional heteroatom selected from oxygen, sulfur or NR₁₅;
R₈ is C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{5-7}$ cycloalkenyl, aryl, arylC$_{1-10}$ alkyl, heteroaryl, heteroarylC$_{1-10}$ alkyl, (CR₁₀R₂₀)$_n$OR₁₁, (CR₁₀R₂₀)$_n$S(O)$_m$R₁₈, (CR₁₀R₂₀)$_n$NHS(O)$_2$R₁₈, (CR₁₀R₂₀)$_n$NR₁₃R₁₄; wherein the aryl, arylalkyl, heteroaryl, heteroaryl alkyl may be optionally substituted;
R₉ is hydrogen, —C(Z)R₁₁ or optionally substituted C$_{1-10}$ alkyl, S(O)$_2$R₁₈, optionally substituted aryl or optionally substituted aryl-C$_{1-4}$ alkyl;
R₁₀ and R₂₀ is each independently selected from hydrogen or C$_{1-4}$ alkyl;
R₁₁ is hydrogen, C$_{1-10}$ alkyl, C$_{3-7}$ cycloalkyl, heterocyclyl, heterocyclyl C$_{1-10}$ alkyl, aryl, arylC$_{1-10}$ alkyl, heteroaryl or heteroarylC$_{1-10}$ alkyl;
R₁₂ is hydrogen or R₁₆;
R₁₃ and R₁₄ is each independently selected from hydrogen or optionally substituted C$_{1-4}$ alkyl, optionally substituted aryl or optionally substituted aryl-C$_{1-4}$ alkyl, or together with the nitrogen to which they are attached form a heterocyclic ring of 5 to 7 members which ring optionally contains an additional heteroatom selected from oxygen, sulfur or NR₉;
R₁₅ is R₁₀ or C(Z)-C$_{1-4}$ alkyl;
R₁₆ is C$_{1-4}$ alkyl, halo-substituted-C$_{1-4}$ alkyl, or C$_{3-7}$ cycloalkyl;
R₁₈ is C$_{1-10}$ alkyl, C$_{3-7}$ cycloalkyl, heterocyclyl, aryl, arylalkyl, heterocyclyl, heterocyclyl-C$_{1-10}$alkyl, heteroaryl or heteroarylalkyl;
R₁₉ is hydrogen, cyano, C$_{1-4}$ alkyl, C$_{3-7}$ cycloalkyl or aryl;
or a pharmaceutically acceptable salt thereof.

Suitably R₁ is a substituted 4-pyridyl or 4-pyrimindyl. More suitably R₁ is substituted by alkoxy, alkylthio, amino, methylarmino, NHRa, or Y. A preferred ring placement of the R₁ substituent on the 4-pyridyl derivative is the 2-position, such as 2-methoxy-4-pyridyl. A preferred ring placement on the 4-pyrimidinyl ring is also at the 2-position, such as in 2-methoxy-pyrimidinyl.

When the substituent is Y, and R$_a$ is aryl, it is preferably phenyl or naphthyl. When R$_a$ is aryl alkyl, it is preferably benzyl or napthylmethyl. When R$_a$ is heterocyclic or heterocyclic alkyl moiety, the heterocyclic portion is preferably pyrrolindinyl, piperidine, morpholino, tetrahydropyran, tetrahydrothiopyranyl, tetrahydrothipyran-sulfinyl, tetrahydrothio-pyransulfonyl, pyrrolindinyl, indole, or piperonyl. It is noted that the heterocyclic rings herein may contain unsaturation, such as in a tryptamine ring.

The aryl, heterocyclic and heteroaryl rings may be optionally substituted one or more times independently with halogen; C$_{1-4}$ alkyl, such as methyl, ethyl, propyl, isopropyl, or t-butyl; halosubstituted alkyl, such as CF₃; hydroxy; hydroxy substituted C$_{1-4}$ alkyl; C$_{1-4}$ alkoxy, such as methoxy or ethoxy; S(O)$_m$ alkyl and S(O)m aryl (wherein m is 0, 1, or 2); C(O)OR$_{11}$, such as C(O)C$_{1-4}$ alkyl or C(O)OH moieties; C(O)R$_{11}$; —OC(O)R$_c$; O—(CH$_2$)s—O—, such as in a ketal or dioxyalkylene bridge, amino; mono- and di-C$_{1-6}$ alkylsubstituted amino; —N(R$_{10}$)C(O)R$_b$; —C(O)NR$_{10}$R$_{20}$; cyano, nitro, or an N-heterocyclyl ring which ring has from 5 to 7 members and optionally contains an additional heteroatom selected from oxygen, sulfur or NR$_{15}$; aryl, such as phenyl; an optionally substituted arylalkyl, such as benzyl or phenethyl; aryloxy, such as phenoxy; or arylalkyloxy such as benzyloxy. Wherein R$_c$ is optionally substituted C$_{1-6}$ alkyl, C$_{3-7}$ cycloalkyl, aryl, arylC$_{1-4}$ alkyl, heteroaryl, heteroarylC$_{1-4}$alkyl, heterocyclyl, or heterocyclclC$_{1-4}$ alkyl moieties.

Preferably, the R$_a$ groups include benzyl, halosubstituted benzyl, napthylmethyl, phenyl, halosubstituted phenyl, aminocarbonylphenyl, alkylphenyl, cyanophenyl, alkylthiophenyl, hydroxyphenyl, alkoxyphenyl, morpholinopropyl, piperonyl, piperidin-4-yl, alkyl substituted piperidine, such as 1-methyl piperidine, or 2,2,6,6-tetramethylpiperidin-4-yl.

Preferably, when the substituent is NHR$_a$ then R$_a$ is aryl, arylalkyl, halosubstituted arylalkyl, halosubstituted aryl, heterocyclic alkyl, hydroxy alkyl, alkyl-1-piperidinecarboxylate, heterocyclic, alkyl substituted heterocyclic, halosubstituted heterocyclic, or aryl substituted heterocyclic. More specifically R$_a$ is benzyl, halosubstituted benzyl, napthylmethyl, phenyl, halosubstituted phenyl, morpholinopropyl, 2-hydroxy ethyl, ethyl-1-piperidinecarboxylate, piperonyl, piperidin-4-yl, alkyl substituted. piperidine, chlorotryptamine, and tetrathiohydropyranyl.

Preferably, when the substituent is a substituted C$_{1-4}$ alkoxy or C$_{1-4}$ alkylthio, the alkyl chain is substituted by halogen, such as fluorine, chlorine, bromine or iodine; hydroxy, such as hydroxyethoxy; C$_{1-10}$ alkoxy, such as a methoxymethoxy, S(O)m alkyl, wherein m is 0, 1 or 2; amino, mono & di-substituted amino, such as in the NR$_7$R$_{17}$ group, i.e. tert-butylaminoethoxy; or where the R$_7$R$_{17}$ may together with the nitrogen to which they are attached cyclize to form a 5 to 7 membered ring which optionally includes an additional heteroatom selected from O/N/S; C$_{1-10}$ alkyl, cycloalkyl, or cycloalkyl alkyl group, such as methyl, ethyl, propyl, isopropyl, t-butyl, etc. or cyclopropyl methyl; or halosubstituted C$_{1-10}$ alkyl. such as CF$_3$. Preferably the R$_1$ substituents are tertbutylaminoethoxy, or hydroxyethoxy.

Suitably, R$_4$ is an optionally substituted phenyl. Preferably the phenyl is substituted one or more times independently by halogen, —SR$_5$, —S(O)R$_5$, —OR$_{12}$, halosubstituted-C$_{1-4}$ alkyl, or C$_{1-4}$ alkyl.

Suitably, R$_2$ is selected from C$_{1-10}$ alkyl, optionally substituted heterocyclyl, optionally substituted heterocyclylC$_{1-10}$ alkyl, (CR$_{10}$R$_{20}$)$_n$NS(O)$_2$R$_{18}$, (CR$_{10}$R$_{20}$)$_n$S(O)$_m$R$_{18}$, arylC$_{1-10}$ alkyl, (CR$_{10}$R$_{20}$)$_n$NR$_{13}$R$_{14}$, optionally substituted C$_{3-7}$cycloalkyl, or optionally substituted C$_{3-7}$cycloalkyl C$_{1-10}$ alkyl. Preferably R$_2$ is morpholino propyl, piperidine, N-methylpiperidine, N-benzylpiperidine, 2,2,6,6-tetramethylpiperidine, 4-aminopiperidine, 4-amino-2,2,6,6-tetramethyl piperidine, 4-hydroxycyclohexyl, 4-methyl-4-hydroxy cyclohexyl, 4-pyrrolinindyl-cyclohexyl, 4-methyl-4-aminocyclohexyl, 4-methyl-4-acetamidocyclohexyl, 4-keto cyclohexyl, 4-oxiranyl, or 4-hydroxy-4-(1-propynyl) cyclohexyl.

Preferably R$_2$ is an optionally substituted heterocyclyl ring, and optionally substituted heterocyclylC$_{1-10}$ alkyl, an optionally substituted C$_{1-10}$ alkyl, an optionally substituted C$_{3-7}$cycloalkyl, an optionally substituted C$_{3-7}$cycloalkyl C$_{1-10}$ alkyl, (CR$_{10}$R$_{20}$)$_n$C(Z)OR$_{11}$ group, (CR$_{10}$R$_{20}$)$_n$NR$_{13}$R$_{14}$, (CR$_{10}$R$_{20}$)$_n$NHS(O)$_2$R$_{18}$, (CR$_{10}$R$_{20}$)$_n$S(O)$_m$R$_{18}$, an optionally substituted aryl; an optionally substituted arylC$_{1-10}$ alkyl, (CR$_{10}$R$_{20}$)$_n$OR$_{11}$, (CR$_{10}$R$_{20}$)$_n$C(Z)R$_{11}$, or (CR$_{10}$R$_{20}$)$_n$C(=NOR$_6$)R$_{11}$ group.

More preferably R$_2$ is an optionally substituted heterocyclyl ring, and optionally substituted heterocyclylC$_{1-10}$ alkyl, optionally substituted aryl, (CR$_{10}$R$_{20}$)$_n$NR$_{13}$R$_{14}$, or (CR$_{10}$R$_{20}$)$_n$C(Z)OR$_{11}$ group.

When R$_2$ is an optionally substituted heterocyclyl, the ring is preferably a morpholino, pyrrolidinyl, or a piperidinyl group. When the ring is optionally substituted, the substituents may be directly attached to the free nitrogen, such as in the piperidinyl group or pyrrole ring, or on the ring itself. Preferably the ring is a piperidine or pyrrole, more preferably piperidine. The heterocyclyl ring may be optionally substituted one to four times independently by halogen; C$_{1-4}$ alkyl; aryl, such as phenyl; aryl alkyl, such as benzyl—wherein the aryl or aryl alkyl moieties themselves may be optionally substituted (as in the definition section below); C(O)OR$_{11}$, such as the C(O)C$_{1-4}$ alkyl or C(O)OH moieties; C(O)H; C(O)C$_{1-4}$ alkyl, hydroxy substituted C$_{1-4}$ alkyl, C$_{1-4}$ alkoxy, S(O)$_m$C$_{1-4}$ alkyl (wherein m is 0, 1, or 2), NR$_{10}$R$_{20}$ (wherein R$_{10}$ and R$_{20}$ are independently hydrogen or C$_{1-4}$alkyl).

Preferably if the ring is a piperidine, the ring is attached to the irnidazole at the 4-position, and the substituents are directly on the available nitrogen, i.e. a 1-Formyl-4-piperidine, 1-benzyl-4-piperidine, 1-methyl-4-piperidine, 1-ethoxycarbonyl-4-piperidine. If the ring is substituted by an alkyl group and the ring is attached in the 4-position, it is preferably substituted in the 2- or 6-position or both, such as 2,2,6,6-tetramethyl-4-piperidine. Similarly, if the ring is a pyrrole, the ring is attached to the imidazole at the 3-position, and the substituents are all directly on the available nitrogen.

When R$_2$ is an optionally substituted heterocyclyl C$_{1-10}$ alkyl group, the ring is preferably a morpholino, pyrrolidinyl, or a piperidinyl group. Preferably this alkyl moiety is from 1 to 4, more preferably 3 or 4, and most preferably 3, such as in a propyl group. Preferred heterocyclic alkyl groups include but are not limited to, morpholino ethyl, morpholino propyl, pyrrolidinyl propyl, and piperidinyl propyl moieties. The heterocyclic ring herein is also optionally substituted in a similar manner to that indicated above for the direct attachment of the heterocyclyl.

When R$_2$ is an optionally substituted C$_{3-7}$cycloalkyl, or an optionally substituted C$_{3-7}$cycloalkyl C$_{1-10}$ alkyl, the cycloalkyl group is preferably a C$_4$ or C$_6$ ring, most preferably a C$_6$ ring, which ring is optionally substituted. The cycloalkyl ring may be optionally substituted one to three times independently by halogen, such as fluorine, chlorine, bromine or iodine; hydroxy; C$_{1-10}$ alkoxy, such as methoxy or ethoxy; S(O)$_m$ alkyl, wherein m is 0, 1, or 2, such as methyl thio, methylsulfinyl or methyl sulfonyl; S(O)$_m$ aryl; cyano, nitro, amino, mono & di-substituted amino, such as in the NR$_7$R$_{17}$ group, wherein R$_7$ and R$_{17}$ are as defined in Formula (I), or where the R$_7$R$_{17}$ may cyclize together with the nitrogen to which they are attached to form a 5 to 7 membered ring which optionally includes an additional heteroatom selected from oxygen, sulfur or NR$_{15}$ (and R$_{15}$ is as defined for Formula (I)); N(R$_{10}$)C(O)X$_1$ (wherein R$_{10}$ is as defined for Formula (I)), and X$_1$ is C$_{1-4}$ alkyl, aryl or arylC$_{1-4}$alkyl); N(R$_{10}$)C(O) aryl; C$_{1-10}$ alkyl, such as methyl, ethyl, propyl, isopropyl, or t-butyl; optionally substituted alkyl wherein the substituents are halogen, (such as CF$_3$), hydroxy, nitro, cyano, amino, mono & di-substituted amino, such as in the NR₇R₁₇ group, S(O)m alkyl and S(O)m aryl, wherein m is 0, 1 or 2; optionally substituted alkylene, such as ethylene or propylene; optionally substituted alkyne, such as ethyne; C(O)OR₁₁ (wherein R₁₁ is as defined in Formula (I)), such as the free acid or methyl ester derivative; the group R_e; —C(O)H; =O; =N—OR₁₁; —N(H)—OH (or substituted alkyl or aryl derivatives thereof on the nitrogen or the oxime moiety); —N(OR_d)—C(O)—R₆'; an optionally substituted aryl, such as phenyl; an optionally substituted arylC₁₋₄alkyl, such as benzyl of phenethyl; an optionally substituted heterocycle or heterocyclic C₁₋₄alkyl, and further these aryl, arylalkyl, heterocyclic, and heterocyclic alkyl moieties are optionally substituted one to two times by halogen, hydroxy, C₁₋₁₀ alkoxy, S(O)_m alkyl, cyano, nitro, amino, mono & di-substituted amino, such as in the NR₇R₁₇ group, an alkyl, halosubstituted alkyl.

Suitably R_d is hydrogen, a pharmaceutically acceptable cation, aroyl or a C₁₋₁₀ alkanoyl group.

Suitably R_e is a 1,3-dioxyalkylene group of the formula —O—(CH₂)_s—O—, wherein s is 1 to 3, preferably s is 2 yielding a 1,3-dioxyethylene moiety, or ketal functionality.

Suitably R₆' is NR₁₉'R₂₀'; alkyl₁₋₆; halosubstituted alkyl₁₋₆; hydroxy substituted alkyl₁₋₆; alkenyl₂₋₆; aryl or heteroaryl optionally substituted by halogen, alkyl₁₋₆, halosubstituted alkyl₁₋₆, hydroxyl, or alkoxy₁₋₆.

Suitably R₁₉' is H or alkyl₁₋₆.

Suitably R₂₀' is H, alkyl₁₋₆, aryl, benzyl, heteroaryl, alkyl substituted by halogen or hydroxyl, or phenyl substituted by a member selected from the group consisting of halo, cyano, alkyl₁₋₂, alkoxy₁₋₆, halosubstituted alkyl₁₋₆, alkylthio, alkylsulphonyl, or alkylsulfinyl; or R₁₉' and R₂₀', may together with the nitrogen to which they are attached form a ring having 5 to 7 members, which members may be optionally replaced by a heteroatom selected from oxygen, sulfur or nitrogen. The ring may be saturated or contain more than one unsaturated bond. Preferably R₆' is NR₁₉'R₂₀', and R₁₉' and R₂₀', are preferably hydrogen.

When the R₂ cycloalkyl moiety is substituted by NR₇R₁₇ group, or NR₇R₁₇ C₁₋₁₀ alkyl group, and the R₇ and R₁₇ are as defined in Formula (I), the substituent is preferably an amino, amino alkyl, or an optionally substituted pyrrolidinyl moiety.

A preferred ring placement on the cycloalkyl moiety is the 4-position, such as in a C₆ ring. When the cycloalkyl ring is di-substituted it is preferably di-substituted at the 4 position, such as in:

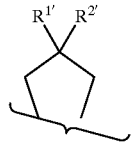

wherein R₁' and R²' are independently the optional substituents indicated above for R₂.

Preferably, R¹' and R²' are hydrogen, hydroxy, alkyl, substituted alkyl, optionally substituted alkyne, aryl, arylalkyl, NR₇R₁₇, and N(R₁₀)C(O)R₁₁. Suitably, alkyl is C₁₋₄ alkyl, such as methyl, ethyl, or isopropyl; NR₇R₁₇ and NR₇R₁₇ alkyl, such as amino, methylamino, aminomethyl, aminoethyl; substituted alkyl such as in cyanomethyl, cyanoethyl, nitroethyl, pyrrolidinyl; aryl such as in phenyl; arylalkyl, such as in benzyl; optionally substituted alkyne, such as ethyne or propynyl; or together R¹' and R²' are a keto functionality.

Preferably R₂ is an optionally substituted heterocyclic, heterocyclic C₁₋₄ alkyl, a cycloalky or a cycloalkyl alkyl.

More preferably R₂ is an optionally substituted C₄ or C₆ cycloalkyl, cyclopropyl methyl, morpholinyl butyl, morpholinyl propyl, morpholinyl ethyl, cyclohexyl substituted by methyl, phenyl, benzyl, amino, acetamide, aminomethyl, aminoethyl, cyanomethyl, cyanoethyl, hydroxy, nitroethyl, pyrrolidinyl, ethynyl, 1-propynyl, =O, O—(CH₂)₂O—, =NOR₁₁, wherein R₁₁ is hydrogen, alkyl or aryl, NHOH, or N(OH)—C(O)—NH₂; or R₂ is morpholinyl propyl, aminopropyl, piperidinyl, N-benzyl-4-piperidinyl, N-methyl-4-piperidinyl, 2,2,6,6-tetramethypiperidinyl, substituted piperidine. such as 1-Formyl-4-piperidine, or a 1-ethoxycarbonyl-4-piperidine.

In all instances herein where there is an alkenyl or alkynyl moiety as a substituent group, the unsaturated linkage, i.e., the vinylene or acetylene linkage is preferably not directly attached to the nitrogen, oxygen or sulfur moieties, for instance in OR₁₃, or for certain R₂ moieties.

As used herein, "optionally substituted", unless specifically defined, shall mean such groups as halogen, such as fluorine, chlorine, bromine or iodine; hydroxy; hydroxy substituted C₁₋₁₀alkyl; C₁₋₁₀ alkoxy, such as methoxy or ethoxy; S(O)m alkyl, wherein m is 0, 1 or 2, such as methyl thio, methylsulfinyl or methyl sulfonyl; amino, mono & di-substituted amino, such as in the NR₇R₁₇ group; or where the R₇R₁₇ may together with the nitrogen to which they are attached cyclize to form a 5 to 7 membered ring which optionally includes an additional heteroatom selected from O/N/S; C₁₋₁₀ alkyl, cycloalkyl, or cycloalkyl alkyl group, such as methyl, ethyl, propyl, isopropyl, t-butyl, etc. or cyclopropyl methyl; halosubstituted C₁₋₁₀ alkyl, such CF₃; an optionally substituted aryl, such as phenyl, or an optionally substituted arylalkyl, such as benzyl or phenethyl, wherein these aryl moieties may also be substituted one to two times by halogen; hydroxy; hydroxy substituted alkyl; C₁₋₁₀ alkoxy; S(O)_m alkyl; amino, mono & di-substituted amino, such as in the NR₇R₁₇ group; alkyl, or CF₃.

Suitable pharmaceutically acceptable salts are well known to those skilled in the art and include basic salts of inorganic and organic acids, such as hydrochloric acid, hydrobromic acid, sulfuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The following terms, as used herein, refer to:

"halo" or "halogens", include the halogens: chloro, fluoro, bromo and iodo.

"C₁₋₁₀alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

The term "cycloalkenyl" is used herein to mean cyclic radicals, preferably of 5 to 8 carbons, which have at least one bond including but not limited to cyclopentenyl, cyclohexenyl, and the like.

The term "alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole.

"heterocyclic" (on its own or in any combination, such as "heterocyclylalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydro pyran, or imidazolidine.

The term "aralkyl" or "heteroarylalkyl" or "heterocyclicalkyl" is used herein to mean $C_{1-4}$ alkyl as defined above attached to an aryl, heteroaryl or heterocyclic moiety as also defined herein unless otherwise indicated.

"sulfinyl"—the oxide S (O) of the corresponding sulfide, the term "thio" refers to the sulfide, and the term "sulfonyl" refers to the fully oxidized $S(O)_2$ moiety.

"aroyl"—a C(O)Ar, wherein Ar is a phenyl, naphthyl, or aryl alkyl derivative such as defined above, such groups include but are not limited to benzyl and phenethyl.

"alkanoyl"—a $C(O)C_{1-10}$ alkyl wherein the alkyl is as defined above.

For the purposes herein the "core" 4-pyrimidinyl moiety for $R_1$ or $R_2$ is referred to as the formula:

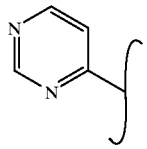

The compounds of the present invention may contain one or more asymmetric carbon atoms and may exist in racemic and optically active forms. All of these compounds are included within the scope of the present invention.

As noted previously, methods of making these compounds can be found in their respective patent applications as noted above.

Compounds of Formula (I) are capable of inhibiting proinflammatory cytokines, such as IL-1, IL-6, IL-8 and TNF.

The compounds of Formula (I) may also be used topically in the treatment or prophylaxis of disease states exacerbated by excessive or inappropriate angiogenesis.

The compounds of Formula (I) are administered in an amount sufficient to inhibit cytokine, in particular IL-1, IL-6, IL-8 or TNF, production such that it is regulated down to normal levels, or in some cases to subnormal levels, so as to ameliorate or prevent the disease state. Abnormal levels of IL-1, IL-6, IL-8 or TNF, for instance in the context of the present invention, constitute: (i) levels of free (not cell bound) IL-1, IL-6, IL-8 or TNF greater than or equal to 1 picogram per ml; (ii) any cell associated IL-1, IL-6, IL-8 or TNF; or (iii) the presence of IL-1, IL-6, IL-8 or TNF mRNA above basal levels in cells or tissues in which IL-1, IL-6, IL-8 or TNF, respectively, is produced.

As used herein, the term "inhibiting the production of IL-1 (IL-6, IL-8 or TNF)" refers to:

a) a decrease of excessive in vivo levels of the cytokine (IL-1, IL-6, IL-8 or TNF) in a human to normal or sub-normal levels by inhibition of the in vivo release of the cytokine by all cells, including but not limited to monocytes or macrophages;

b) a down regulation, at the genomic level, of excessive in vivo levels of the cytokine (IL-1, IL-6, IL-8 or TNF) in a human to normal or sub-normal levels;

c) a down regulation, by inhibition of the direct synthesis of the cytokine (IL-1, IL-6, IL-8 or TNF) as a postranslational event; or d) a down regulation, at the translational level, of excessive in vivo levels of the cytokine (IL-1, IL-6, IL-8 or TNF) in a human to normal or sub-normal levels.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells, however, also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

A new member of the MAP kinase family, alternatively termed CSBP, p38, or RK, has been identified independently by several laboratories recently. Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors of the present invention, compounds of Formula (I) have been determined to be potent and selective inhibitors of CSBP/p38/RK kinase activity. These inhibitors are of aid in determining the signaling pathways involvement in inflammatory responses. In particular, for the first time a definitive signal transduction pathway can be prescribed to the action of lipopolysaccharide in cytokine production in macrophages. In addition to those diseases already noted, treatment of stroke, neurotrauma, cardiac and renal reperfusion injury, thrombosis, glomerulonephritis, diabetes and pancreatic β cells, multiple sclerosis, muscle degeneration , eczema, psoriasis, sunburn, and conjunctivitis are also included.

The cytokine inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) *Arthritis Rheum.* 31:1406–1412; Badger, et al., (1989) *Circ. Shock* 27, 51–61; Votta et al., (1994)in vitro. *Bone* 15, 533–538; Lee et al., (1993). *B Ann. N. Y. Acad. Sci.* 696, 149–170.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the Formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably include a surface active agent. The resulting solution may then be clarified by filtration, transferred to a suitable container which is then sealed and sterilized by autoclaving or maintaining at 98–100 C for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen will be from about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

Chronic diseases which have an inappropriate angiogenic component are various ocular neovasularizations, such as diabetic retinopathy and macular degeneration.

Other chronic diseases which have an excessive or increased proliferation of vasculature are tumor growth and metastasis, atherosclerosis, and certain arthritic conditions. Therefore cytokine inhibitors will be of utility in the blocking of the angiogenic component of these disease states.

The term "excessive or increased proliferation of vasculature inappropriate angiogenesis" as used herein includes, but is not limited to, diseases which are characterized by hemangiomas and ocular diseases.

The term "inappropriate angiogenesis" as used herein includes, but is not limited to, diseases which are characterized by vesicle proliferation with accompanying tissue proliferation, such as occurs in cancer, metastasis, arthritis and atherosclerosis.

Described below a model of inflammatory angiogenesis is used to show that cytokine inhibition will stop the tissue destruction of excessive or inappropriate proliferation of blood vessels. Based on these observations, a cytokine inhibitor, 1-Piperidine-4-(4-fluorophenyl)-5-(2-aminopyrimidin-4-yl)imidazole—Compound I was tested for its ability to inhibit angiogenesis in an in vivo animal model of inflammatory angiogenesis.

The murine airpouch granuloma model of chronic inflammation (Kimura et al., 1985, J. Pharmacobio-Dyn., 8:393–400; Colville-Nash et al.,1995, J. Pharm. and Exp. Ther., 274:1463–1472) whose disclosure is incorporated herein by reference in its entirety, is characterized by inflammatory cell influx, fibrous tissue proliferation and intense angiogenesis. It is representative of inflammatory angiogenesis and demonstrates that the angiogenic component can be pharmacologically modulated independently of granuloma growth and size. In addition, angiogenesis can be accurately quantitated by a vascular casting method.

Figure 1B:
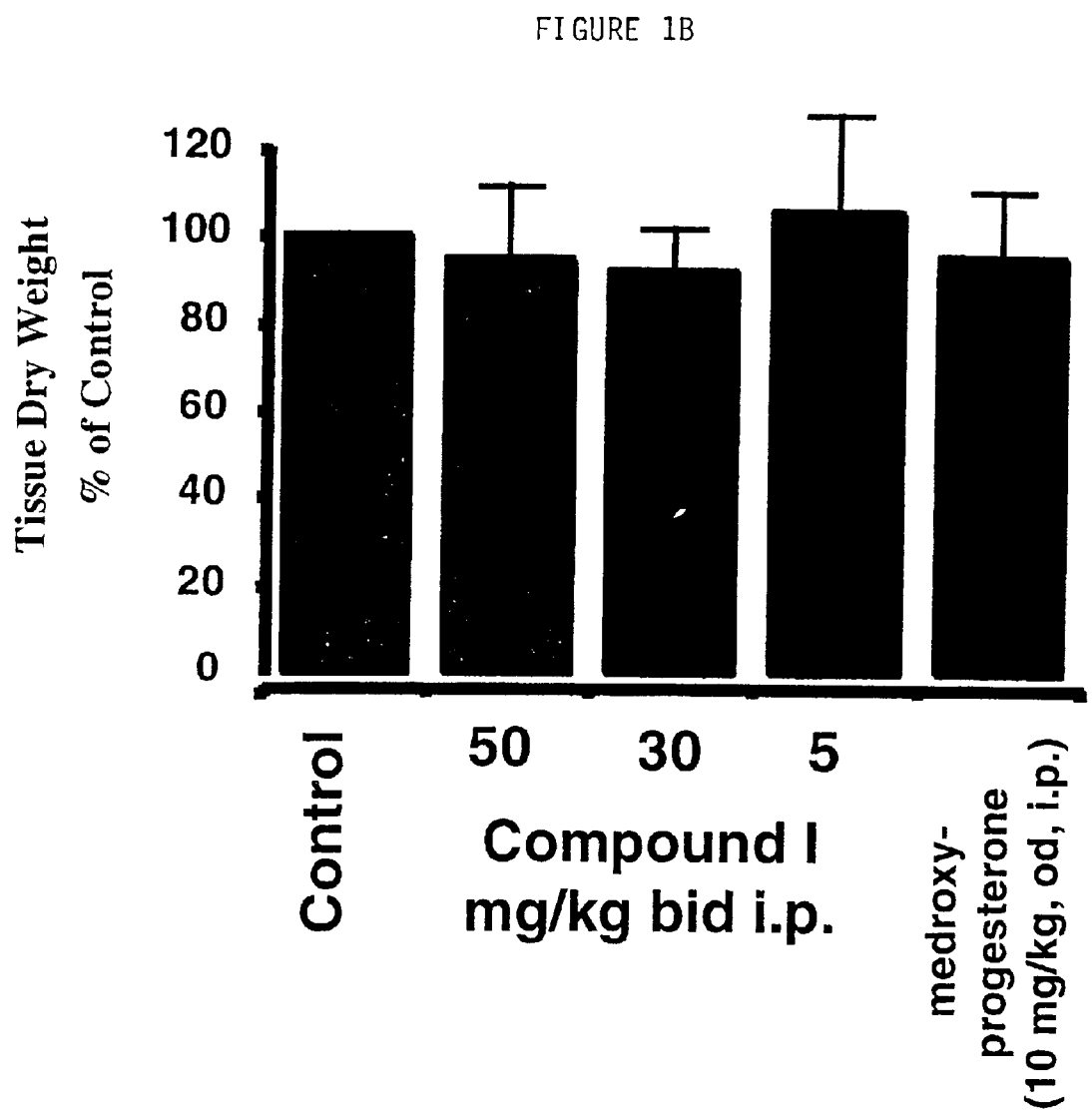

The effect of the compound on vascular density (and dry weight) was measured for 6 days after induction of the granuloma. (FIGS. 1a and 1b) This time point has been determined to be at or near the peak of angiogenesis. Compound I demonstrated a significant and dose dependent decrease in the vascular index with a maximum reduction of 44% at 50 mg.kg, bid, i.p. As a positive control medroxyprogesterone, an angiostatic steroid (Gross et al., 1981, Proc. Natl. Acad. Sci. USA, 78:1176–1180)—whose disclosure is hereby incorporated by reference in its entirety, was utilized. This control demonstrated a maximum reduction of 50% in this model. Neither Compound I nor medroxyprogesterone had an effect on granuloma size as measured by dry weight.

Angiogenesis in the granuloma was microscopically evaluated. The vasculature of day 6 granulomas from both untreated and compound I treated mice was examined. The profound angiogenesis in the granuloma is demonstrated by the extensive vascular network in the control tissue. There was a striking reduction in the vasculature of the treated tissue. In fact, there was a almost no fine capillaries visible, only a few larger vessels.

Figure 2A:
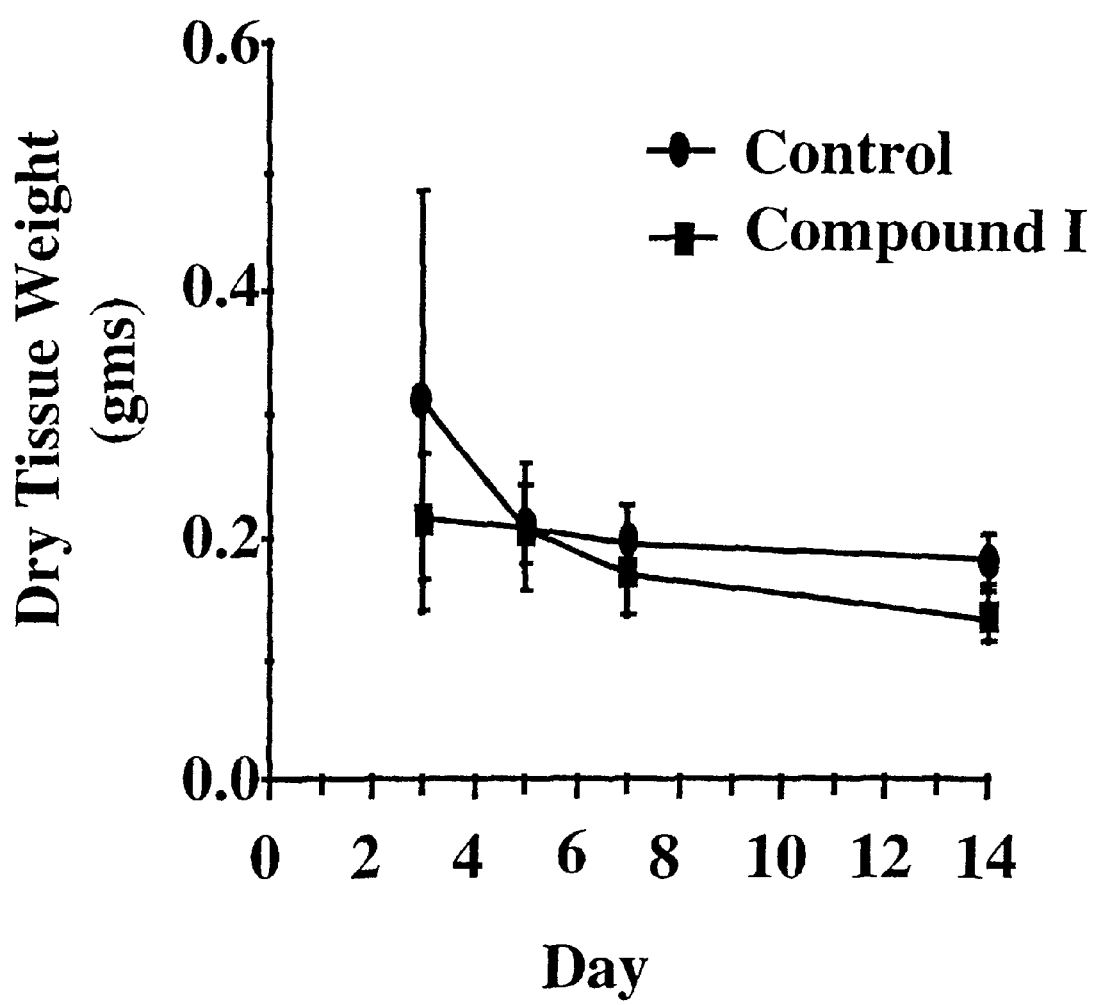
Figure 2C:
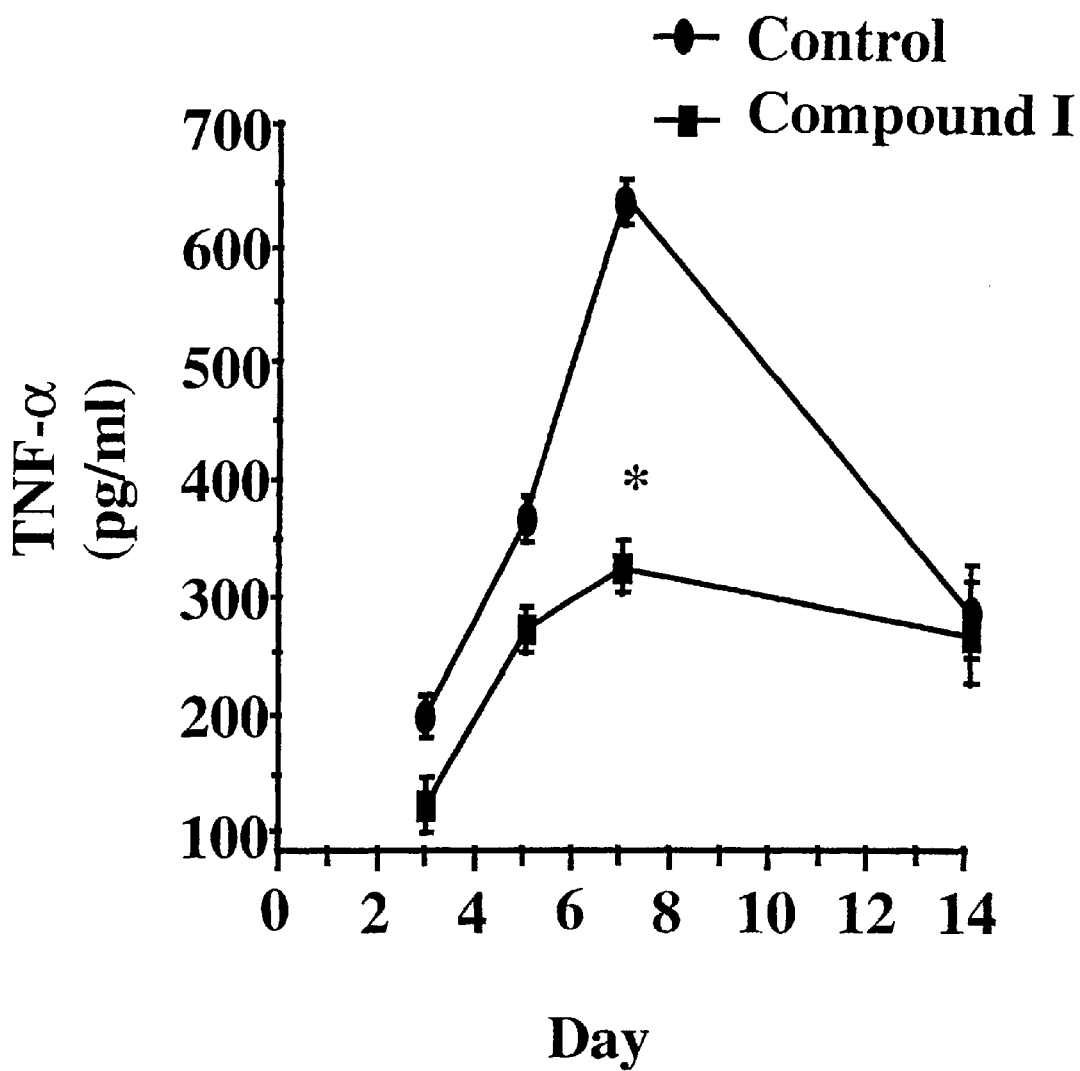
Figure 2D:
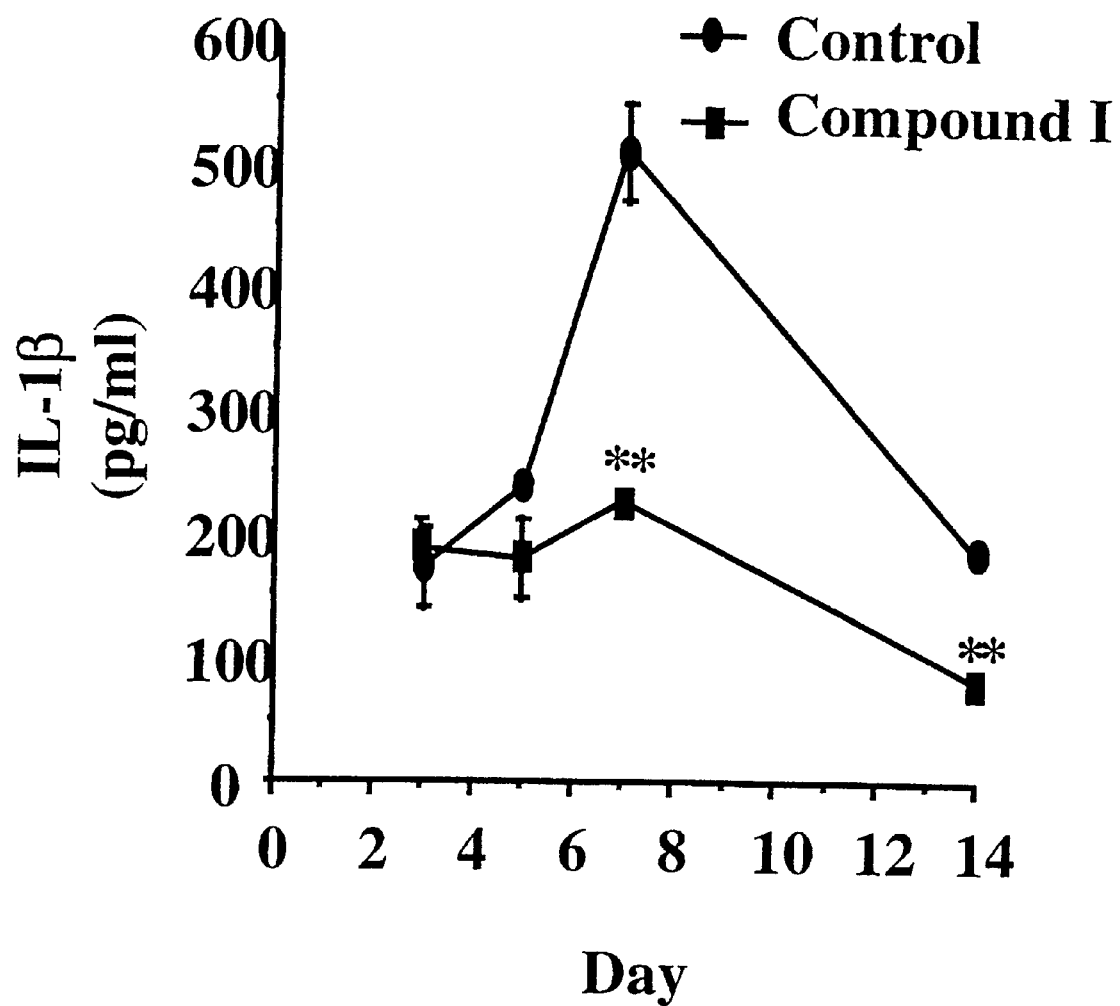

The effect of the compound on angiogenesis was also evaluated at several time points, to determine if its effects would be different at the various stages of inflammatory and angiogenic progression. Compound I was given orally, at an intermediate dose of 30 mg/kg twice a day starting on day 0, and granulomas were evaluated on days 3, 5, 7, and 14. Granuloma size remained fairly constant and was unaffected by the compound (FIG. 2). The VI of the control group rose gradually from day 3 to 14, whereas the VI of the treated group remained level. At day 3, the compound did not cause a significant reduction in VI compared to control, however, at days 5, 7, and 14, the VI was lowered significantly. Thus the compound did not affect the initial burst of angiogenesis, but did prevent the increase in angiogenesis which occurs following day 3.

Inflammatory cytokines such as IL-1β and TNF-α have been implicated in the pathogenesis of angiogenesis in chronic inflammation, and the compound has been demonstrated to inhibit the synthesis of these cytokines. The levels of these cytokines over the course to granuloma development were measured to determine if the modulation of their expression by the compound correlated with angiogenesis. Cytokine levels were measured by ELISA using homogenates of granuloma tissue. TNF-α levels rose sharply, peaking at day 7 and dropping back down to moderate levels by day 14 (FIG. 2). Compound I greatly reduced TNF-α levels at day 7. IL-β levels were also high in control granulomas, peaking at day 7, and as with TNF-α, the compound effectively blocked the increased IL-1β expression. Thus, the ability of the compound to block the sharp rise in TNF-α and IL-1β between days 5 and 7 correlated well with the ability of the compound to prevent the increase in vascular index that occurs over the same time points.

Methods

Murine air pouch granuloma model

Day-1, mice are anesthetized using Aerrane (isoflurane) gas (5%), after which 3mls of air is injected into the dorsal subcutaneous tissue using a 27 g needle. Mice are allowed to recover.

Day 0, mice are again anesthetized using Aerrane, once anesthetized 0.5 ml of Freunds complete adjuvant with 0.1% v/v croton oil is injected into the air pouch formed on Day-1. The animals also begin their dosing regime (number of days dependent upon study) with the animals typically receiving compound in 0.2 ml N,N, Dimethyl Acetoacetamide(DMA) (Sigma, St. Louis, Mo.)/Cremephor El (Sigma, St. Louis, Mo.)/saline (10/10/80) or other appropriate vehicle. The animals are allowed to recover and all subsequent dosing is performed on the animals in the absence of anesthetics.

Days 1–5, animals are dosed according to schedule.

On Day 6 the animals are again anesthetized using Aerrane after which a vascular cast is made (Kimura et al., 1986, J.Pharmacobio-Dyn., 9:442–446), this involves a 1 ml tail vein i.v. injection of a Carmine Red(10%)(Sigma, St. Louis, Mo.)/gelatin (5%)(Sigma, St. Louis, Mo.) solution. The animals are then sacrificed by lethal dose of anesthesia and chilled at 4 C for 2 hours prior to the removal of the granuloma tissue.

When the granuloma is removed it is weighed and then dried for 3 days at 45 C and reweighed. The dried tissue is then digested in 0.9 ml of a 0.05M phosphate buffer pH 7.0 containing 12 U/ml$^{-1}$ papain (Sigma, St. Louis, Mo.) and 0.33 g/L$^{-1}$ N-acetyl-1-Cysteine (Sigma, St. Louis, Mo.) at 57 C for 3 days. After 3 days digestion the carmine red is solubilized by the addition of 0.1 ml 5 mM NaOH. Samples are centrifuged and then filtered using 0.2 um acrodiscs. The carmine content is then determined against a carmine red standard curve (0.5 to 2 mg/ml) generated in extracted tissue from non carmine treated animals and read at 490 nm. Sample and standard values are determined using DeltaSoft Elisa analysis software (Biometallics Inc., Princeton, N.J.). The carmine content is then used to determine the vascular indexes for the various treatments, vascular index being the mg carmine dye/gm dry tissue.

Tissue extracts were made by homogenizing granulomas in 0.5 ml 5 mM $KH_2PO_4$/0.1 gm wet tissue. IL-1β levels were determined using a Cytoscreen Immunoassay Kit (catalog #KMC 0012) from BioSource International, Camarillo, Calif. TNF-α levels were determined using the following assay: plates were coated with hamster anti-murine TNF-α antibody (Genzyme, Cambridge, Mass.), for 2 hours at 37° C., washed and blocked with a casein-BSA solution (5 gram/L for each) for 1 hour at 37° C., the samples were added and incubated at 4° C. overnight. Plates were washed, and the secondary antibody, Rabbit Anti-mouse TNF-α (Genzyme), was added for 2 hours at 37° C., the plates were washed, and the tertiary antibody Goat Anti-rabbit peroxidase conjugate (BioSource International, Camarillo, Calif.) was added for 2 hours at 37° C. The plates were then washed, and substrate OPD (Sigma) was added for 20 minutes at room temperature. The reaction was terminated with 25 ul 0.1M NaF per well, the O.D. read at 460 nm. Sample values for both ELISAs are calculated using DeltaSoft ELISA analysis software (Biomettalics Inc., Princeton, N.J.).

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A method of treating a chronic disease in a mammal in need thereof, which disease is characterized by excessive, undesired or inappropriate angiogenesis, with an effective amount of a compound of Formula (I) which inhibits the production, transcription or translation of a cytokine, which cytokine is inhibited by inhibition of the kinase CSBP/p38/RK:

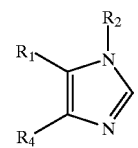

wherein:
$R_1$ is 4-pyridyl, pyrimidinyl, quinolyl, isoquinolinyl, quinazolin-4-yl, 1-imidazolyl or 1-benzimidazolyl ring, which ring is optionally substituted independently one to three times with Y, $NHR_a$, optionally substituted $C_{1-4}$ alkyl, halogen, hydroxyl, optionally substituted $C_{1-4}$ alkoxy, optionally substituted $C_{1-4}$ alkylthio, $C_{1-4}$ alkylsulfinyl, $CH_2OR_{12}$, amnino, mono and di-$C_{1-6}$ alkyl substituted amino, or $N(R_{10})C(O)R_b$;

Y is $OR_a$;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, $C(Z)NR_7R_{17}$, $C(Z)OR_{16}$, $(CR_{10}R_{20})_vCOR_{12}$, $SR_5$, $SOR_5$, $OR_{12}$, halo-substituted-$C_{1-4}$ alkyl, $C_{1-4}$ alkyl, $ZC(Z)R_{12}$, $NR_{10}C(Z)R_{16}$, or $(CR_{10}R_{20})_vNR_{10}R_{20}$ and which, for other positions of substitution, is halogen, cyano, $C(Z)NR_{13}R_{14}$, $C(Z)OR_3$, $(CR_{10}R_{20})_{m''}COR_3$, $S(O)_mR_3$, $OR_{13}$, halo-substituted-$C_{1-4}$ alkyl, $C_{1-4}$ alkyl, $(CR_{10}R_{20})_{m''}NR_{10}C(Z)_3$, $NR_{10}S(O)_mR_8$, $NR_{10}S(O)_{m'NR7}R_{17}$, $ZC(Z)_3$ or $(CR_{10}R_{20})_{m''}NR_{13}R_{14}$;

v is 0, or an integer having a value of 1 or 2;

m is 0, or the integer 1 or 2;

m' is an integer having a value of 1 or 2, m" is 0, or an integer having a value of 1 to 5;

$R_2$ is $(CR_{10}R_{20})_{n'}OR_9$, heterocyclyl, heterocyclyl$C_{1-10}$ alkyl, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl$C_{1-10}$alkyl, aryl, aryl$C_{1-10}$ alkyl, heteroaryl, heteroaryl$C_{1-10}$alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$, $(CR_{10}R_{20})_nNO_2$, $(CR_{10}R_{20})_nCN$, $(CR_{10}R_{20})_{n'}SO_2R_{18}$, $(CR_{10}R_{20})_nS(O)_{m'}NR_{13}R_{14}$, $(CR_{10}R_{20})_nC(Z)R_{11}$, $(CR_{10}R_{20})_nOC(Z)R_{11}$, $(CR_{10}R_{20})_nC(Z)OR_{11}$, $(CR_{10}R_{20})_nC(Z)NR_{13}R_{14}$, $(CR_{10}R_{20})_nC(Z)NR_{11}OR_9$, $(CR_{10}R_{20})_nNR_{10}C(Z)R_{11}$, $(CR_{10}R_{20})_nNR_{10}C(Z)NR_{13}R_{14}$, $(CR_{10}R_{20})_nN(OR_6)C(Z)NR_{13}R_{14}$, $(CR_{10}R_{20})_nN(OR_6)C(Z)R_{11}$, $(CR_{10}R_{20})_nC(=NOR_6)R_{11}$, $(CR_{10}R_{20})_nNR_{10}C(=NR_{19})NR_{13}R_{14}$, $(CR_{10}R_{20})_nOC(Z)NR_{13}R_{14}$, $(CR_{10}R_{20})_nNR_{10}C(Z)NR_{13}R_{14}$, $(CR_{10}R_{20})_nNR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl; wherein the aryl, arylalkyl, heteroaryl, heteroaryl alkyl, heterocyclic and heterocyclic alkyl groups may be optionally substituted;

n is an integer having a value of 1 to 10;

n' is 0, or an integer having a value of 1 to 10;

Z is oxygen or sulfur;

$R_a$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl, wherein each of these moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;

$R_3$ is heterocyclyl, heterocyclylC$_{1-10}$ alkyl or $R_8$;

$R_5$ is hydrogen, C$_{1-4}$ alkyl, C$_{2-4}$ alkenyl, C$_{2-4}$ alkynyl or NR$_7$R$_{17}$, excluding the moieties —SR$_5$ being —SNR$_7$R$_{17}$ and —SOR$_5$ being —SOH;

$R_6$ is hydrogen, a pharmaceutically acceptable cation, C$_{1-10}$ alkyl, C$_{3-7}$ cycloalkyl, aryl, arylC$_{1-4}$ alkyl, heteroaryl, heteroarylC$_{1-4}$ alkyl, heterocyclic, aroyl, or C$_{1-10}$ alkanoyl;

$R_7$ and $R_{17}$ is each independently selected from hydrogen or C$_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or NR$_{15}$;

$R_8$ is C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{5-7}$ cycloalkenyl, aryl, arylC$_{1-10}$ alkyl, heteroaryl, heteroarylC$_{1-10}$ alkyl, (CR$_{10}$R$_{20}$)$_n$OR$_{11}$, (CR$_{10}$R$_{20}$)$_n$S(O)$_m$R$_{18}$, (CR$_{10}$R$_{20}$)$_n$NHS(O)$_2$R$_{18}$, (CR$_{10}$R$_{20}$)$_n$NR$_{13}$R$_{14}$; wherein the aryl, arylalkyl, heteroaryl, heteroaryl alkyl may be optionally substituted;

$R_9$ is hydrogen, —C(Z)R$_{11}$ or optionally substituted C$_{1-10}$ alkyl, S(O)$_2$R$_{18}$, optionally substituted aryl or optionally substituted aryl-C$_{1-4}$ alkyl;

$R_{10}$ and $R_{20}$ is each independently selected from hydrogen or C$_{1-4}$ alkyl;

$R_{11}$ is hydrogen, C$_{1-10}$ alkyl, C$_{3-7}$ cycloalkyl, heterocyclyl, heterocyclyl C$_{1-10}$alkyl, aryl, arylC$_{1-10}$ alkyl, heteroaryl or heteroarylC$_{1-10}$ alkyl;

$R_{12}$ is hydrogen or $R_{16}$;

$R_{13}$ and $R_{14}$ is each independently selected from hydrogen or optionally substituted C$_{1-4}$ alkyl, optionally substituted aryl or optionally substituted aryl-C$_{1-4}$ alkyl, or together with the nitrogen to which they are attached form a heterocyclic ring of 5 to 7 members which ring optionally contains an additional heteroatom selected from oxygen, sulfur or NR$_9$;

$R_{15}$ is $R_{10}$ or C(Z)-C$_{1-4}$ alkyl;

$R_{16}$ is C$_{1-4}$ alkyl, halo-substituted-C$_{1-4}$ alkyl, or C$_{3-7}$ cycloalkyl;

$R_{18}$ is C$_{1-10}$ alkyl, C$_{3-7}$ cycloalkyl, heterocyclyl, aryl, arylalkyl, heterocyclyl, heterocyclyl-C$_{1-10}$alkyl, heteroaryl or heteroarylalkyl;

$R_{19}$ is hydrogen, cyano, C$_{1-4}$ alkyl, C$_{3-7}$ cycloalkyl or aryl; or a pharmaceutically acceptable salt thereof.

2. The method according to claim 1 wherein $R_1$ is a substituted 4-pyridyl or 4-pyrimidinyl.

3. The method according to claim 1 wherein $R_a$ is aryl, arylalkyl, halosubstituted arylalkyl, halosubstituted aryl, heterocyclic alkyl, hydroxy alkyl, alkyl-1-piperidinecarboxylate, heterocyclic, alkyl substituted heterocyclic, halosubstituted heterocyclic, or aryl substituted heterocyclic.

4. The method according to claim 3 wherein $R_a$ is benxyl, halosubstituted benzyl, napthylmethyl, phenyl, halosubstituted phenyl, morpholinopropyl, 2-hydroxy ethyl, ethyl-1-piperidinecarboxylate, piperonyl, piperidin-4-yl, alkyl substituted piperidine, chlorotryptamine, and tetrathiohydropyranyl.

5. The method according to claim 1 wherein $R_4$ is an optionally substituted phenyl.

6. The method according to claim 1 wherein $R_2$ is selected from optionally substituted heterocylcyl, optionally substituted heterocyclylC$_{1-10}$ alkyl, (CR$_{10}$R$_{20}$)$_n$NS(O)$_2$R$_{18}$, (CR$_{10}$R$_{20}$)$_n$S(O)$_m$R$_{18}$, arylC$_{1-10}$ alkyl, (CR$_{10}$R$_{20}$)$_n$NR$_{13}$R$_{14}$, optionally substituted C$_{3-7}$cycloalkyl, or optionally substituted C$_{3-7}$cycloalkyl C$_{1-10}$ alkyl.

7. The method according to claim 6 wherein $R_2$ is morpholino propyl, piperidine, N-methylpiperidine, N-benzylpiperidine, 2,2,6,6-tetramethylpiperidine, 4-aminopiperidine, 4-amino-,2,6,6-tetramethyl piperidine, 4-hydroxycyclohexyl, 4-methyl-4-hydroxy cyclohexyl, 4-pyrrolinindyl-cyclohexyl, 4-methyl-4-arninocyclohexyl, 4-methyl-4-acetamidocyclohexyl, 4-keto cyclohexyl, 4-oxiranyl, or 4-hydroxy-4-(1-propynyl)cyclohexyl.

8. The method according to claim 1 wherein the cytokine is IL-1β.

9. The method according to claim 1 wherein the cytokine is TNF-α.

10. The method according to claim 1 wherein the disease is diabetic retinopathy and other ocular neovascularizations.

11. The method according to claim 1 wherein the disease is tumor growth and metastasis.

* * * * *